United States Patent
Zickler et al.

(10) Patent No.: US 9,603,702 B2
(45) Date of Patent: Mar. 28, 2017

(54) INTRAOCULAR LENSES FOR MANAGING GLARE, ADHESION, AND CELL MIGRATION

(71) Applicant: Abbott Medical Optics Inc., Santa Ana, CA (US)

(72) Inventors: Leander Zickler, Menlo Park, CA (US); Rakhi Jain, Fort Worth, TX (US); Jim Deacon, Goleta, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 73 days.

(21) Appl. No.: 14/065,137

(22) Filed: Oct. 28, 2013

(65) Prior Publication Data
US 2014/0052245 A1    Feb. 20, 2014

Related U.S. Application Data (63) Continuation of application No. 11/534,200, filed on Sep. 21, 2006, now Pat. No. 8,568,478.

(51) Int. Cl.
*A61F 2/16*    (2006.01)
*H04W 52/14*    (2009.01)
(Continued)

(52) U.S. Cl.
CPC ......... *A61F 2/1613* (2013.01); *H04W 52/146* (2013.01); *H04W 52/367* (2013.01);
(Continued)

(58) Field of Classification Search
CPC .. A61F 2/16; A61F 2/1613; A61F 2/47; A61F 2002/161; A61F 2002/1605;
(Continued)

(56) References Cited

U.S. PATENT DOCUMENTS

| | | |
|---|---|---|
| 3,988,068 A | 10/1976 | Sprague |
| 4,343,050 A | 8/1982 | Kelman |

(Continued)

FOREIGN PATENT DOCUMENTS

| | | |
|---|---|---|
| EP | 246754 A1 | 11/1987 |
| WO | WO-0119290 A1 | 3/2001 |
| WO | WO-03037225 A1 | 5/2003 |

OTHER PUBLICATIONS

International Preliminary Report on Patentability and Written Opinion for Application No. PCT/US07/078781, mailed on Mar. 24, 2009, 7 pages.

(Continued)

*Primary Examiner* — Christopher D Prone
*Assistant Examiner* — Rokhaya Diop
(74) *Attorney, Agent, or Firm* — Abbott Medical Optics Inc.

(57) ABSTRACT

An intraocular lens for providing vision to a subject contains an optic, a support structure coupled to the optic. The intraocular lens also includes a textured surface and/or subsurface layer. The optic is disposed about an optical axis and comprises an anterior surface and an opposing posterior surface, the surfaces being configured to focus light when implanted within an eye having a capsular bag. The textured surface is disposed over a surface portion of the intraocular lens. The subsurface layer is configured to scatter an amount of light that is at least twice the amount of light scattered by portions of the material adjacent the subsurface layer or at least twice the amount of light scattered by another intraocular lens that does not have the subsurface layer, but which is otherwise substantially equivalent.

27 Claims, 6 Drawing Sheets

(51) Int. Cl.
*H04W 52/36* (2009.01)
*A61F 2/00* (2006.01)

(52) U.S. Cl.
CPC . *A61F 2002/009* (2013.01); *A61F 2002/1681* (2013.01); *A61F 2250/0053* (2013.01); *A61F 2250/0098* (2013.01)

(58) Field of Classification Search
CPC ...... A61F 2002/1696; A61F 2002/1689; A61F 2/1694; A61F 2002/1681; A61F 2250/0053; A61F 2250/0098; A61F 2002/009; H04W 52/146; H04W 52/367
USPC .. 623/4.1, 6.11, 6.16, 6.17, 6.52, 6.56, 6.19, 623/6.27–6.31, 6.37–6.41
See application file for complete search history.

(56) References Cited

U.S. PATENT DOCUMENTS

| | | | |
|---|---|---|---|
| 4,449,257 A | 5/1984 | Koeniger | |
| 4,605,409 A | 8/1986 | Kelman | |
| 4,676,791 A | 6/1987 | LeMaster et al. | |
| 4,808,181 A * | 2/1989 | Kelman | 623/6.43 |
| 4,863,466 A | 9/1989 | Schlegel | |
| 4,863,470 A | 9/1989 | Carter | |
| 4,955,909 A | 9/1990 | Ersek et al. | |
| 4,995,715 A | 2/1991 | Cohen | |
| 5,002,571 A | 3/1991 | O'Donnell et al. | |
| 5,203,790 A * | 4/1993 | McDonald | 623/6.17 |
| 5,219,361 A | 6/1993 | Von Recum et al. | |
| 5,405,385 A * | 4/1995 | Heimke et al. | 623/6.4 |
| 5,755,786 A | 5/1998 | Woffinden et al. | |
| 6,027,531 A | 2/2000 | Tassignon | |
| 6,129,759 A | 10/2000 | Chambers | |
| 6,264,692 B1 | 7/2001 | Woffinden et al. | |
| RE37,585 E | 3/2002 | Mourou et al. | |
| 6,558,419 B1 | 5/2003 | Pham et al. | |
| 6,592,621 B1 | 7/2003 | Domino | |
| 6,632,887 B2 | 10/2003 | LeBoeuf et al. | |
| 6,638,307 B2 | 10/2003 | Valyunin et al. | |
| 6,648,741 B2 | 11/2003 | Schneider | |
| 6,656,222 B2 | 12/2003 | Young et al. | |
| 6,857,744 B2 | 2/2005 | Nakada et al. | |
| 6,884,262 B2 | 4/2005 | Brady et al. | |
| RE38,839 E | 10/2005 | Magnante | |
| 6,997,554 B2 | 2/2006 | Nakada et al. | |
| 7,014,656 B2 | 3/2006 | Galin | |
| 2001/0034552 A1 * | 10/2001 | Young et al. | 623/6.16 |
| 2001/0041935 A1 * | 11/2001 | Valyunin | A61F 2/1602 623/6.56 |
| 2002/0026239 A1 | 2/2002 | Schachar | |
| 2003/0093083 A1 | 5/2003 | Peyman | |
| 2004/0002290 A1 * | 1/2004 | Green | 451/29 |
| 2004/0039446 A1 | 2/2004 | McNicholas | |
| 2004/0184158 A1 | 9/2004 | Shadduck | |
| 2004/0188872 A1 * | 9/2004 | Jani | 264/1.32 |
| 2005/0021139 A1 * | 1/2005 | Shadduck | 623/6.35 |
| 2005/0021140 A1 | 1/2005 | Liao | |
| 2005/0033422 A1 * | 2/2005 | Zhao et al. | 623/6.17 |
| 2005/0154456 A1 | 7/2005 | Brady et al. | |
| 2005/0177231 A1 * | 8/2005 | Ricci et al. | 623/6.16 |

OTHER PUBLICATIONS

International Preliminary Report on Patentability and Written Opinion for Application No. PCT/US07/078784, mailed on Mar. 24, 2009, 6 pages.
International Search Report for Application No. PCT/US07/078781, mailed on Feb. 5, 2008, 3 pages.
International Search Report for Application No. PCT/US07/078784, mailed on Feb. 6, 2008, 2 pages.
Matsushima H., et al., "Active Oxygen Processing for Acrylic Intraocular Lenses to Prevent Posterior Capsule Opacification," Journal of Cataract and Refractive Surgery, 2006, vol. 32 (6), pp. 1035-1040.
Zickler L., et al ., "Ferntosecond All-Solid-State Laser for Refractive Surgery," Proceedings of SPIE, 2003, vol. 4978 (2003), pp. 194-207.

* cited by examiner

INTRAOCULAR LENSES FOR MANAGING GLARE, ADHESION, AND CELL MIGRATION

CROSS-REFERENCE TO RELATED APPLICATIONS

The present application is a continuation application of U.S. application Ser. No. 11/534,200 filed on Sep. 21, 2006, now U.S. Pat. No. 8,568,478, which is incorporated herein by reference in its entirety.

BACKGROUND OF THE INVENTION

Field of the Invention

This invention relates generally to an intraocular lens and more specifically to an intraocular lens configured to reduce glare, improve adhesion to the eye, and/or mitigate unwanted cell migration such as posterior capsule opacification (PCO).

Description of the Related Art

The implantation of intraocular lenses represents one of the safest surgical procedures currently conducted and enjoys an extremely high success rate. One common use of intraocular lenses is for the replacement of natural lenses that have become clouded due to the formation of cataracts. Intraocular lenses have also found other uses, for example in the form of anterior chamber lenses that are implanted just behind the cornea in order to restore vision to patients that are extremely myopic or hyperopic.

One set of problems that are frequently encountered in the use of intraocular lenses is that of glare and posterior capsule opacification (PCO). Glare problems can occur due to edge effects from the implanted optic, which is typically much smaller than the natural lens being replaced. For example peripheral light entering the eye can be redirected by the edges of the optic, or even haptic portions connected to the optic, back toward the central portion of the field of view to create annoying and even dangerous glare images that are superimposed with the normal image formed by the center of the optic.

PCO typically occurs as a result of cells (epithelial cells) that migrate from the equatorial regions of the capsular bag into the optic portion of the intraocular lens. When this occurs, the result can be a loss of vision that is similar to that caused by the cataractous material that precipitated the surgery in the first place.

Another problem that may occur when an intraocular lens is implanted into an eye is that of poor adhesion of the intraocular lens to the eye, for example, poor adhesion to the capsule walls of a capsular bag into which the intraocular lens is placed. Good adhesion between the intraocular lens and the capsular bag can, for example, help maintain centration of the lens about the optical axis. In addition, good adhesion about the periphery of an optic may, at least in part, be important for reducing migration of epithelial cells toward the center of the optic. Adhesion can be particularly important in accommodating intraocular lenses, since these types of lenses typically require that force from the ciliary muscles and the capsular bag be effectively transferred to the intraocular lens so that the lens can translate or deform when changing between accommodative and disaccommodative states.

Various methods and device designs have been used to handle the duo of maladies common to intraocular lens implants. Examples include those disclosed in U.S. Pat. Nos. 6,162,249; 6,468,306; and 6,884,262, and U.S. Patent Application Number 2005/033422, all of which are herein incorporated by reference.

In some cases a solution for one of these two problems may actually exacerbate the other. For example, sharp corner edges about the periphery have been found to generally reduce the problem of PCO; however, such discontinuities may also have the unwanted effect of increasing glare due to the scatter of entering the intraocular lens from the peripheral field of view.

Further improvements and design options are needed for reducing the problems of both glare and PCO in patients receiving intraocular lens implants, as well as increase the adhesion of intraocular lens implants to the capsular bag.

SUMMARY OF THE INVENTION

The present invention is broadly directed to devices and methods that may be used to reduce the problems of glare and PCO common to intraocular lenses and/or other ophthalmic devices such as capsular rings. Embodiments of the present invention are also generally directed to structures that enhance the ability of an intraocular lens to adhere or bond to the eye, for example, to the capsule walls of a capsular bag. Using embodiments of the current invention, each of these problems may be addressed in such a way that the solution to one of these problems does not exacerbate or augment the other problem. For instance, an intraocular lens comprising an optic and a support structure coupled to the optic may be configured with one or more textured surfaces comprising a plurality of periodically-spaced protrusions, each protrusion having a smooth distal face and at least one sharp corner edge configured to engage a capsule wall of the capsular bag and/or at least one cell disposed along the capsule wall. In certain embodiments, the textured surface may be configured to reduce glare effects produced by light interacting with the peripheral edge of an optic or a portion of a haptic. For example, the dimensions and/or spacing of the protrusions may be selected to diverge or scatter incident light and/or to produce optical interference.

In some embodiments, the texture surface comprises a plurality of channels or grooves separated by a plurality of smooth ridges. In other embodiments, the textured surface comprises a plurality of pillars that are periodically disposed along the surface in one or two dimensions. In yet other embodiments, the textured surface comprises a plurality of rings that are concentrically disposed about an optical axis of the intraocular lens. In some embodiments, the textured surface comprises a contiguous smooth surface with a plurality of periodically-spaced wells disposed along the smooth surface, wherein a plurality of sharp corner edges are formed at a plurality of intersections between the smooth surface and the wells. The textured surface may be configured to control or maintain cells (e.g., epithelial cells) that come into contact with the textured surface in a favorable state. A favorable cell state of the cells may include a state in which the cells closely adhere to the textured surface or a state in which cell proliferation or propagation is mitigated by maintaining the cell in a form in which they are more contented and less likely to divide to produce more cells (e.g., when the cells are in a more spindle-like form, and not in a more spherical form). In addition, the textured surface may be configured to provide adhesion directly between the capsular bag and the textured surface, even where no epithelial cells are present. The improved adhesion provided by the textured surface, either directly or indirectly (e.g., via epithelial cells remaining on the capsule walls), may provide enhanced stabilization and centration of the intraocular lens.

In some embodiments, improved adhesion is used to enhance the so-called "shrink wrap" effect produced as the capsular walls adhere to one another in the vicinity of the intraocular lens. This improved adhesion and the tendency of cells in contact with the textured surface to not proliferate, either alone or in combination, advantageously permits the textured surface to be used to reduce the problem of PCO. Also, the improved adhesion provided by the textured surface may be of particular importance in accommodating intraocular lenses in which forces of the entire capsular bag need to be transmitted to the intraocular lens in an evenly distributed manner.

The textured surface may be disposed along any portion of the intraocular lens where attachment to the capsular bag or cell growth management is desired. The textured surface may be used in conjunction with mono-focal lenses, multi-focal lenses, or accommodating lenses, for example, to cause a structural element of the intraocular lens to remain attached to the capsular bag during accommodative movement thereof. In some embodiments, a cellular mono-layer is formed that is able to impede or prevent the migration of cells beyond the mono-layer.

In certain embodiments, the intraocular lens is alternatively or additionally configured with a subsurface layer that is disposed within an interior region of the intraocular lens that is configured to reduce glare effects produced by incident light. The subsurface layer may be located, for example, within a periphery of the optic between a top surface and a bottom surface or inside a portion of a haptic that is attached to the optic. Preferably, the subsurface layer is configured to scatter light, for example, to scatter an amount of light that is at least twice the amount of light scattered by material adjacent the subsurface layer. In some embodiments, the subsurface layer is a subsurface mark that may be, for example, a symbol, one or more alphanumeric characters, or reticle. Such a subsurface mark may be used to show an orientation and/or position of the intraocular lens, to identify the intraocular lens, and/or to provide one or more characteristics of the intraocular lens (e.g., the focal length of the intraocular lens).

The subsurface layer may be produced using a plasma that is generated within the internal region of the intraocular lens and that forms a plurality of localized micro-discontinuities having refractive indices differing from the refractive index of material adjacent the subsurface layer. The plasma may be created, for example, by using a laser to create a laser-induced optical breakdown (LIOB) condition.

Since the subsurface layer is located inside the intraocular lens and is isolated from the outer surfaces of the intraocular lens, it may be specifically structured to address glare issues with no negative impact on cell migration. Conversely, the channels discussed above may be configured independent of their potential impact on glare, since a subsurface layer may be configured to scatter or redirect light impinging on the channels.

Thus, embodiments of the present invention may be used, in effect, to decouple the solutions to the problems of PCO and glare. In certain embodiments, only one of the two solutions discussed above need be incorporated, since the remaining problem in such cases either is not particularly critical or is solved using a different approach or solution.

Additional aspects, features, and advantages of the present invention are set forth in the following description and claims, particularly when considered in conjunction with the accompanying drawings in which like parts may bear like reference numbers.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures.

DETAILED DESCRIPTION OF THE DRAWINGS

Embodiments of the invention are generally directed to intraocular lenses for implantation within the posterior chamber or capsular bag of an eye; however, novel embodiments of the invention may also be applied, where appropriate, to intraocular lenses in general (e.g., a phakic intraocular lens located in the anterior chamber or a corneal implant located within the cornea) or to other ophthalmic devices (e.g., contact lenses or a capsular ring).

Referring to FIGS. 1-4, an intraocular lens 100 according to an embodiment of the present invention is illustrated that advantageously addresses the dual problems of unwanted cell migration (e.g., PCO) and glare. The intraocular lens 100 comprises an optic 102 disposed about an optical axis OA and has an anterior surface 104 and an opposing posterior surface 108. The surfaces 104, 108 are configured to focus light onto the retina of an eye into which the intraocular lens 100 is placed. The intraocular lens 100 further comprises a support structure 109 and a periphery or peripheral region 110 disposed about the optical axis OA that includes a top surface 112, a bottom surface 114, and a subsurface layer 120 disposed between the top surface and bottom surfaces 112, 114. As discussed in greater detail below, the subsurface layer 120 may be configured to advantageously scatter or otherwise redirect incident light so as to reduce glare on the retina of an eye into which the intraocular lens 100 is placed. The subsurface layer 120 may also be configured for other uses such as for marking the intraocular lens 100 for identification or providing a practitioner information regarding the orientation or position of the intraocular lens 100.

Figure 1:
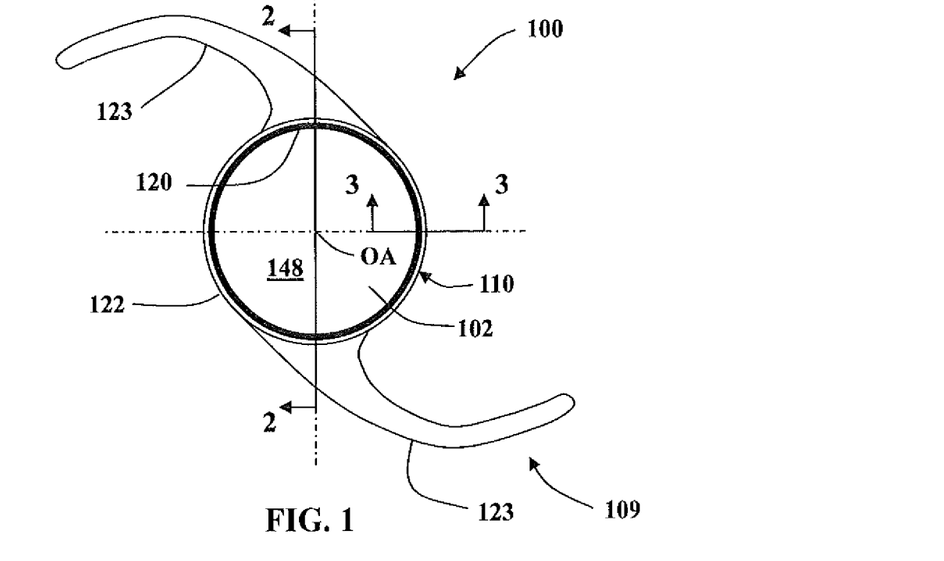
FIG. 1 is a top view of an intraocular lens according to an embodiment of the present invention illustrating an anterior side of an optic and a peripheral region that includes a subsurface layer disposed below a surface of the intraocular lens.
Figure 2:
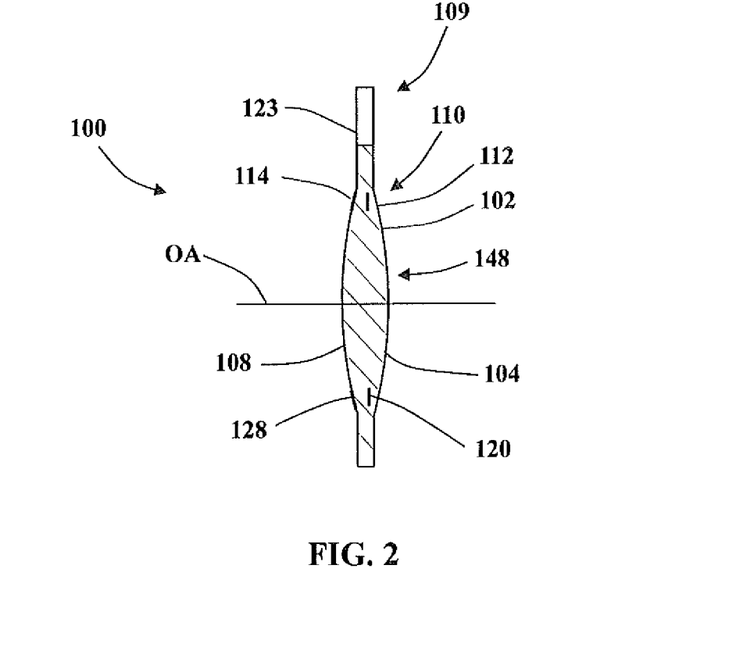
FIG. 2 is a cross-sectional side view of the intraocular lens illustrated in FIG. 1 across a section 2-2.
Figure 3:
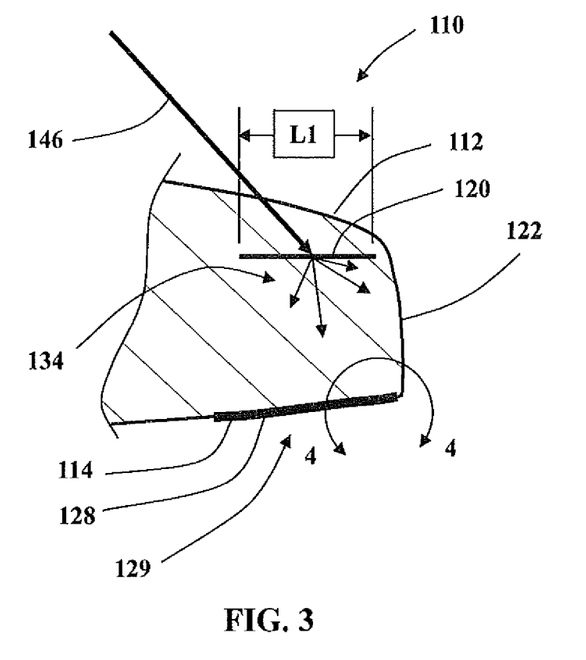
FIG. 3 is a magnified side view of the intraocular lens illustrated in FIG. 1 across a section 3-3.

The peripheral region 110 may also include an outer surface 122 that is disposed substantially parallel to the optical axis OA. The outer surface 122 may be straight, arcuate, or some combination thereof when viewed in cross-section in a plane congruent with the optical axis OA. In some embodiments, the outer surface 122 is also configured to reduce glare and/or PCO, for example, as disclosed in U.S. Pat. No. 6,884,262.

In the illustrated embodiment, the support structure 109 comprises two haptics 123. The haptics 123 may be used to center the intraocular lens 100 within the eye of a subject and are generally constructed to minimize damage to eye. In some embodiments, the support structure is more complex than that shown in the FIG. 1. In certain embodiments, the support structure includes a structure that is configured to fill or substantially fill a capsular bag and/or to provide accommodative action.

Figure 4:
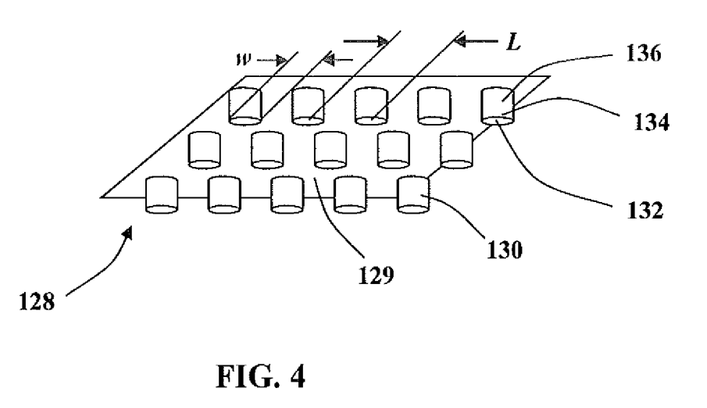
FIG. 4 is a further magnified side view of the intraocular lens illustrated in FIG. 3 illustrating the details of a structured surface for promoting capsular adhesion, optical control, and/or control of cellular growth.
Figure 5:
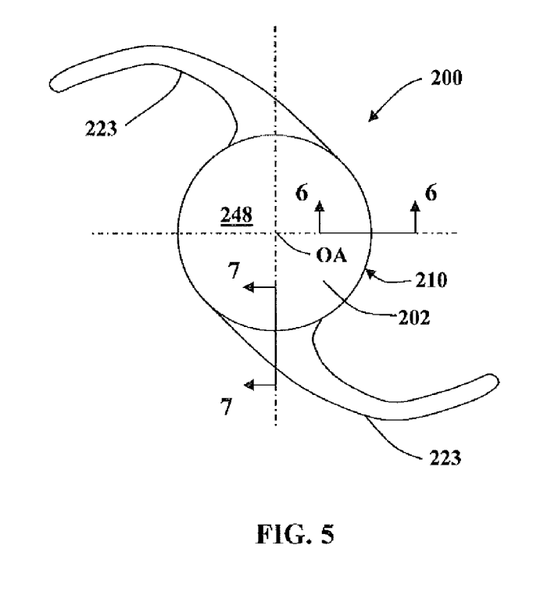
FIG. 5 is a top view of an intraocular lens according to another embodiment of the invention.

Referring to FIGS. 3-4, the intraocular lens 100 further comprises a textured surface 128 disposed over a surface portion 129. The textured surface 128 may be advantageously configured to address the problems of cell migration and/or glare. For example, the textured surface 128 may be configured to maintain cells coming into contact with the textured surface 128 in a favorable state that prevents or reduces proliferation and/or propagation of cells beyond the boundary of the textured surface 128. Alternatively or additionally, the textured surface 128 may be advantageously configured to adhere to the walls of a capsular bag by adhering to the epithelial cells that remain on the capsule surface after the natural lens of the eye has been removed. In certain embodiments, the structured surface 128 is configured to provide adhesion directly with the capsule wall, even where no or few epithelial cells are present. While the textured surface is located on the periphery 110 of the optic 102, it may be disposed on any surface of the intraocular lens 100, including the optic 102.

The textured surface 128 comprises a plurality of periodically-spaced protrusions 130, each protrusion 130 having a smooth distal face 132 and at least one sharp corner edge 134 configured to engage a wall of the capsular bag (not illustrated) of a subject and/or at least one cell disposed along the capsule wall. The protrusions extend from the surface portion by an amount that is between about 0.1 micrometer and about 2 micrometers, preferably between 0.3 micrometers and 1 micrometer, more preferably by about 0.5 micrometers, In certain embodiments, the textured surface 128 is configured to reduce glare effects produced by light interacting with the optic 102, the periphery 110, and/or the support structure 109. For example, the dimensions and/or spacing of the protrusions 130 may be selected to diverge or scatter incident light and/or to produce optical interference. Also, in some embodiments, while the smooth distal faces 132 are generally smooth, the roughness or structure of the surface portion 129 may be selected to be rough or otherwise structured to produce a predetermined characteristic, for example, to scatter or redirect light incident thereon so as to reduce glare.

The sharp corner edges 134 preferably have a radius that is less than about 200 nanometers, more preferably less than 100 nanometers, and even more preferably less than 20 nanometers. The radius of the corners formed between the support structure 109 and the protrusions 130 may be substantially equal to those of the sharp edge corners 134. However, the radius of these corners may be greater than those of the sharp edge corners 134 without adverse affect, for example, in order to increase the manufacturability of the structured surface 128.

The smooth distal faces 132 generally have an RA surface roughness that is less than about 200 nanometers, preferably less than 50 nanometers, even more preferably less than about 20 nanometers. The roughness of the other surfaces of the textured surface 128 (e.g., the surface portion 129) may be greater than that of the smooth distal faces 132.

In the illustrated embodiment, the plurality of protrusions 130 comprises a plurality of pillars and the smooth distal faces 132 are circular; however, other shapes and configurations of the protrusions 130 are possible (e.g., smooth distal faces 132 may be rectangular, oval, or some other shape; the protrusions 130 may be configured to form concentric rings, as discussed below herein). Each protrusion 130 may further comprise a side wall 136, such that the sharp corner edge 134 is formed along an intersection of the side wall 136 and the smooth distal face 132. The sharp corner edges 134 are generally substantially perpendicular to the smooth distal face 132. The side walls 136 and the smooth distal faces 132 form an angle that is generally between about 60 degrees and about 120 degrees and is preferably about 90 degrees.

Each smooth distal face 132 has a width w and is disposed along the surface portion 129 with a center-to-center spacing L between adjacent distal faces 132. The width w is generally between about 1 micrometer and about 10 micrometers, preferably between 1 micrometer and 5 micrometers, and even more preferably between 1 micrometer and 4 micrometers. The ratio of the width w to the center-to-center spacing L is generally between about 0.4 and about 0.7, with a ratio of about 0.5 being preferable in certain embodiments. In some embodiments, for example, when the center-to-center spacing is relatively large, the ratio of the width w to the center-to-center spacing L may be as great as 0.8 or more.

In some embodiments, the textured surface 128 comprises an essentially inverse pattern to that illustrated in FIG. 4. That is to say, the textured surface 128 may comprise a contiguous smooth surface with a plurality of periodically-spaced wells or voids disposed along the smooth surface in one or more directions. In such embodiments, a plurality of sharp corner edges are formed at the intersections between the smooth surface and the wells.

The textured surface 128 may be disposed at various locations upon an intraocular lens according to embodiments of the present invention. For example, referring to FIGS. 5-8, an intraocular lens 200 comprises an optic 202, a pair of haptics 223, and a periphery or peripheral region 210. The intraocular lens 200 further comprises a textured surface 228 that may be disposed both within the peripheral region 210 and along at least a portion of the haptics 223 adjacent the peripheral region 210. The textured surface 228 may run contiguously between the peripheral region 210 and haptics 223, as illustrated in FIG. 8. Alternatively or additionally, one or more textured surfaces 228' (not shown) may be formed on one or more portions of the haptics 223 that are separate from the textured surface 228 formed within the peripheral region 210. In some embodiments, the textured surface 228' is formed on the haptics 223 and there is no textured surface formed within the peripheral region 210.

Figure 6:
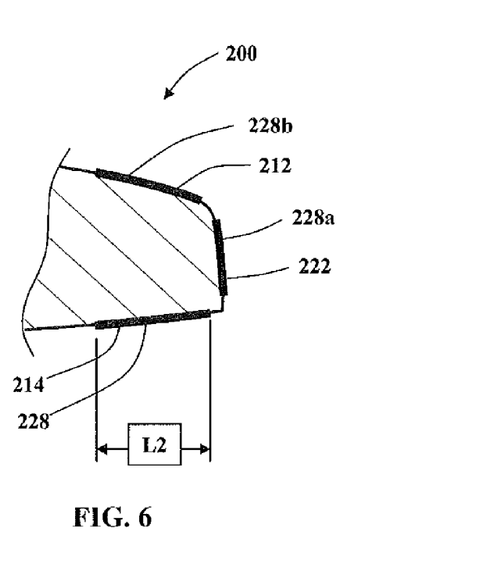
FIG. 6 is a magnified side view of the intraocular lens illustrated in FIG. 5 across a section 6-6.

The intraocular lens 200 further comprises a textured surface 228a disposed on outer surface 222 of the periphery 210 and a textured surface 228b disposed on an anterior surface 212 of the optic 202. The additional textured surfaces 228a, 228b may be used to further provide adhesion between the capsular bag and the intraocular lens 200, for example, by causing the anterior capsule to adhere to the anterior surface of the peripheral region 210. The textured surfaces 228, 228a, and/or 228b may be separated from one another (as illustrated in FIG. 6) or be contiguous with one another to form a single textured surface. One or more of the textured surfaces 228, 228a, 228b may form an annular ring that completely surrounds the center of the optic 202. Alternatively, one or more of the textured surfaces 228, 228a, 228b form an annular ring that is broken at predetermined locations.

Figure 7:
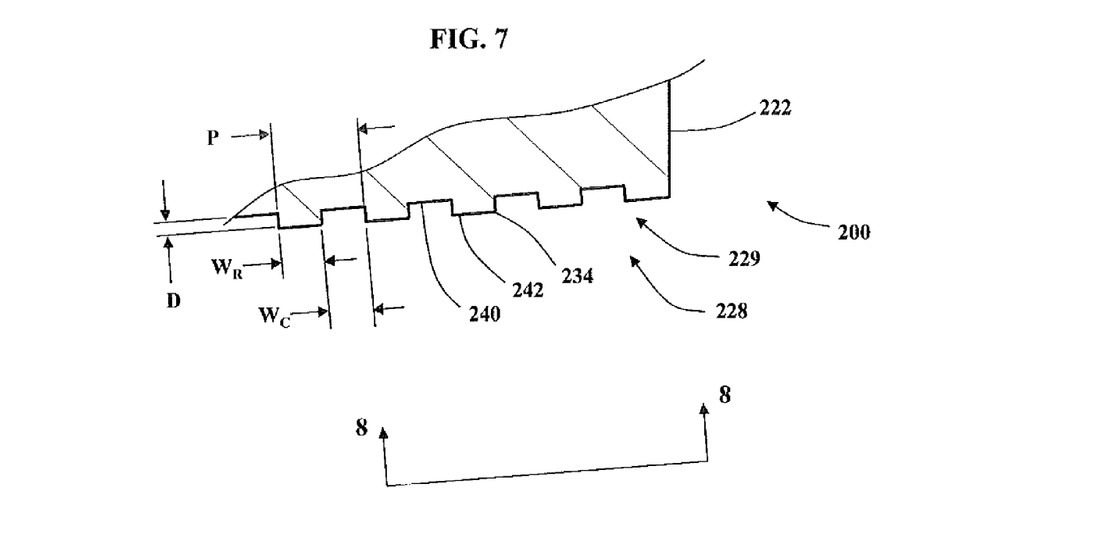
FIG. 7 is a magnified side view of the intraocular lens illustrated in FIG. 5 across a section 7-7.
Figure 8:
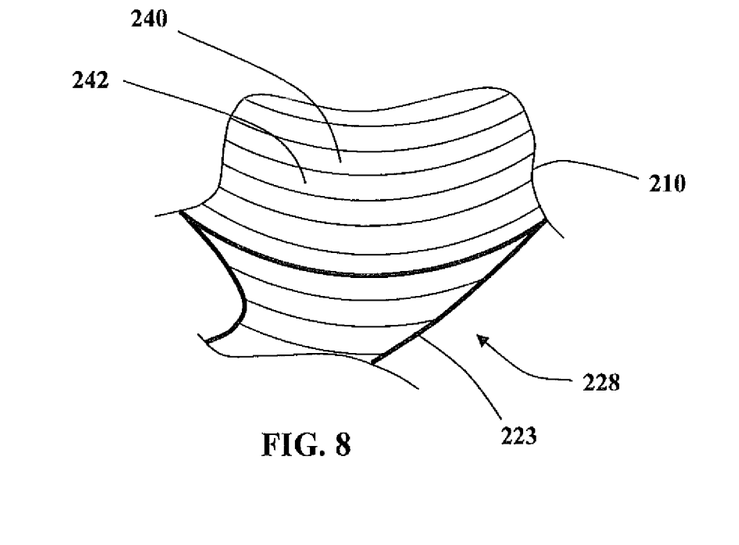
FIG. 8 is a bottom view of the intraocular lens illustrated in FIG. 7.

Referring to FIGS. 7-8, textured surface 228 comprises a plurality of equally-spaced channels or grooves 240 separated by a plurality of smooth ridges 242. The smooth ridges 242 are generally smooth so as to maintain cells in a favorable state, reduce glare, and/or to provide adhesion between the intraocular lens 200 and a capsular bag. The textured surface 228 may be used alone or in combination with a subsurface layer such as the subsurface layer 120 in order to reduce or eliminate both PCO on the optic 202 and the formation of glare patterns on the retina of the eye due to light entering the eye from peripheral fields of view.

In some embodiments, the textured surface 228 completely surrounds the central portion 248 of the optic 202. In such embodiments, the textured surface 228 may form a mono-layer of cells that may act as a barrier that is effective in impeding or completely preventing the migration of epithelial cells inside the optic 202 when the intraocular lens 200 is implanted into the eye of a subject. Alternatively, the channels 240 may be configured radially or with some orientation or pattern, while the overall shape of the textured surface 228 is disposed circumferentially about the optic 202.

In the illustrated embodiment shown in FIGS. 7-8, the textured surface 228 is circumferentially disposed about the optic 202 and has an over all radial length L2 that is greater than about 100 micrometers and less than about 1 millimeter. In some embodiments, the radial length L2 is less than 100 micrometer or greater than 1 millimeter. For example, the radial length L2 may be greater than 1 millimeter, so as to increase adhesion or prevent propagation of cellular growth onto the posterior surface 208 of the optic 202. In the illustrated embodiment, the textured surface 228 is disposed entirely and continuously about the optic 202 on a surface portion 229 that follows the general form or contour of the intraocular lens 200 in the vicinity of the textured surface 228. The surface portion 229 may be flat, curved, or arcuate in shape.

The channels 240 have depth D, a width $W_C$, and may be disposed periodically with a period P. The depth D of the channels 240 is generally less than about 2 micrometer, in some instances preferably less than or equal to about 0.5 micrometer. The width $W_C$ of the channels 240 and a width $W_R$ of the smooth ridges 242 is generally between about 1 micrometer and about 10 micrometers, preferably between 1 micrometer and 5 micrometers, and even more preferably between 1 micrometer and 4 micrometers. The ratio of the width $W_R$ of the smooth ridges 242 to the period spacing L is generally between about 0.4 and about 0.7, with a ratio of about 0.5 being preferable in certain embodiments. In some embodiments, for example, when the center-to-center spacing is relatively large, ratio of the width w to the center-to-center spacing L may be as great as 0.8 or more.

The smooth ridges 242 generally have an RA surface roughness that is less than about 200 nanometers, preferably less than 50 nanometers, even more preferably less than about 20 nanometers. The roughness of the other surfaces of the textured surface 228 may be greater than that of the smooth ridges 242.

The walls of the channels 240 preferably intersect the smooth ridges to form sharp edge corners 234. The sharp corner edges 234 preferably have a radius that is less than about 200 nanometers, more preferably less than 100 nanometers, and even more preferably less than 20 nanometers. The radius of the corners formed between the walls of the channels 240 and the bottom of the channels 240 may be substantially equal to those of the sharp edge corners 234; however, the radius of these corners may be greater than those of the sharp edge corners 134 without adverse affect, for example, in order to increase the manufacturability of the structured surface 228.

It will be appreciated that the geometry and dimensions discussed in relation to any one of the textured surfaces 128, 228, 228a, or 228b may, where appropriate, also be applied to any one of the other textured surfaces 128, 228, 228a, or 228b, or any other embodiment of a textured surface according to the present invention.

Textured surfaces according to embodiments of the present invention may be used in accommodating intraocular lenses, for example, to provide adhesion between the support structure or positioning member of an intraocular lens and the walls of the capsular bag. Such accommodating intraocular lenses are disclosed, for example, in U.S. Pat. Nos. 6,488,708, 6,494,911, or 6,761,737, and in U.S. Patent Application Publication Numbers 2004/0082994 and 2004/0111153, which are all herein incorporated by reference. In an exemplary embodiment illustrated in FIG. 9, a bag filling accommodating intraocular lens 300 comprises a flexible positioning member 301 coupled to an optic 302. The flexible positioning member 301 has an outer surface 304 configured to engage the capsular bag so as to produce accommodation in response to an ocular force. As used herein, the term "ocular force" means any force produced by the eye of a subject that stresses, moves, or changes the shape of an optic or intraocular lens that is placed in the eye of a subject. The ocular force acting on a lens may be produced, for example, by the state or configuration of the ciliary body (e.g., contracted or retracted), changes in the shape of the capsular bag of the eye, stretching or contraction of one or more zonules, vitreous pressure changes, and/or movement of some part of the eye such as the ciliary body, zonules, or capsular bag, either alone or in combination.

Figure 9:
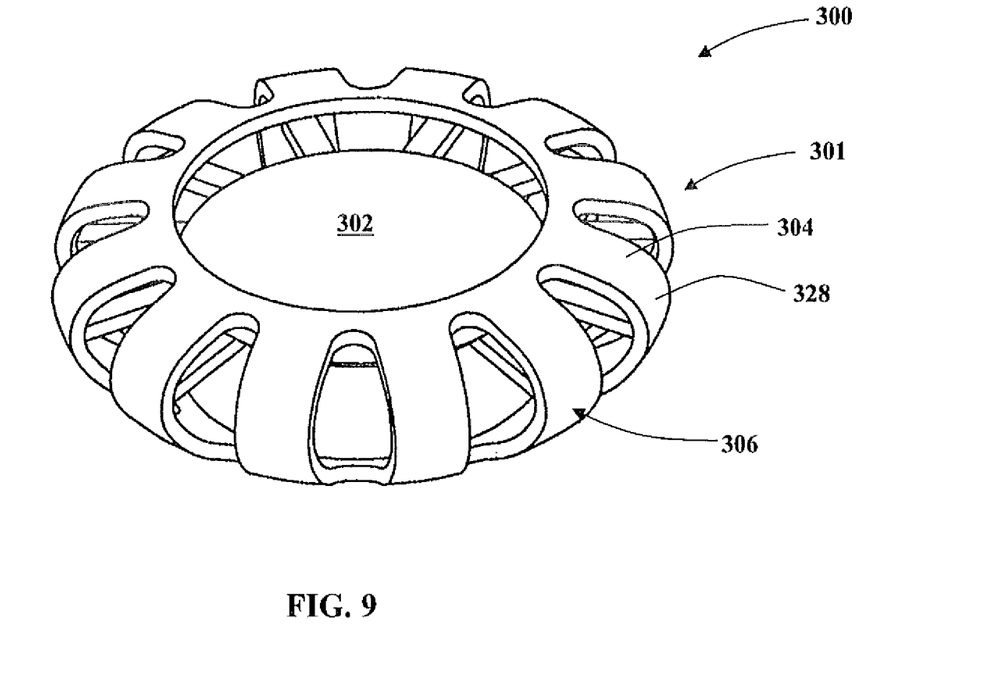
FIG. 9 is a perspective view of an accommodating intraocular lens according to an embodiment of the present invention.

The textured surface 328 may be disposed over substantially the entire outer surface 304, as illustrated in FIG. 9. Alternatively, the textured surface may be applied only over predetermined portions of the outer surface 304, such that portions of the outer surface 304 are able to slide against the capsular bag as it changes between accommodative and disaccommodative states. For example the textured surface 328 may be selectively disposed along an equatorial region 306.

The textured surface 328 is generally configured to produce adhesion between the capsular bag and the positioning member 301 so that ocular forces produced by the eye (e.g., by the capsular bag) may be effectively transferred to the positioning member 301 in such a way that optic 302 is translated and/or deformed to produce a predetermined amount of change in optical power. It will be appreciated that sufficient adhesion to the capsular is generally important for enabling and controlling both the amount of accommodation and the quality of resultant image produced as the optic 302 changes between accommodative and disaccommodative states.

A textured surface according to the present invention may also be applied to at least portions of the surface of an intraocular lens having essentially no haptics or positioning member. For example, as will be appreciated by one of ordinary skill in the art, the textured surface may be applied to at least a portion of an outer surface of a flexible bag or bladder of an intraocular lens, wherein the bladder is filled with a resilient fill material. An example of such an intraocular lens is illustrated in FIG. 14 of U.S. Patent Application Publication Number 2004/0082993, which is herein incorporated by reference. The textured surface may be applied to specific portions of the outer surface, for example, about an equatorial portion of the flexible bag. Alternatively, the textured surface may be applied over large portions of the flexible bag, for example, over all areas of the outer surface of the flexible bag that are to contact the walls of a capsular bag into which the intraocular lens is to be placed. In any event, the textured surface generally covers a sufficient portion of the flexible bag to permit the intraocular lens to deform in conformance with deformations of the capsular bag as it changes between accommodative and disaccommodative states.

The textured surfaces 128, 228, 228a, 228b may be produced using one or more of a variety of known fabrication methods. For simplicity, fabrication methods discussed herein are with reference to the textured surface 128; however, it will be appreciated that such methods may also be applied in the formation of the textured surfaces 228, 228a, 228b, 328, or other textured surfaces according to embodiments of the present invention. In some embodiments, the textured surface 128 is produced by chemically etching the periodically-spaced protrusions 130 along the surface portion 129. In such embodiments, a mask may be disposed over the surface portion 129 to provide a plurality of exposed areas thereon. One or more chemicals may be subsequently used to etch material from the exposed areas. In other embodiments, a protective film is disposed upon the mask and exposed areas of the surface portion 129. The mask may then be removed and a subsequent chemical treatment used to from the textured surface 128 by etching material from portions of the surface portion 129 not protected by the protective film. In yet other embodiments, a laser similar to that used in forming the subsurface layer 120 is used to etch or form the textured surface 128.

Alternatively or in addition to etching material to from the surface portion 129, material may be deposited onto the surface portion 129 in forming the textured surface 128. For example, the protrusions 130 illustrated in FIG. 4 may be formed by applying one or more layers onto the surface portion 129 (e.g., using a chemical vapor deposition process). In some embodiments, the textured surface 128 is formed by an embossing process or by machining the desired features from the surface portion 129, for example, by using a CNC lathe with milling capabilities. In other embodiments, the textured surface 128 is formed by molding or by a combination of machining and molding.

When an intraocular lens according to embodiments of the present invention has both a textured surface 128 and one or more subsurface layers 120, the textured surface 128 may be formed either before or after formation of the subsurface layer 120. In some embodiments, the textured surface 128 is disposed directly above or below the subsurface layer 120, for example within the peripheral region 110 surrounding the optic 102.

Referring again to FIGS. 1-3, the subsurface layer 120 may be used to reduce glare potentially caused by light that might otherwise be reflected by the periphery 110 and redirected toward the central field of view of the eye. As illustrated in FIG. 3, the subsurface layer 120 is configured to produce diffuse or scattered light 134 when illuminated by a beam of light 146. In general, the amount of scattered light 134 may be characterized by a scattering cross-section that indicates the amount of light from an incident beam that is scattered by the subsurface layer 120. As shown in the illustrated embodiment, the subsurface layer 120 may be circumferentially disposed entirely about a central portion 148 of the optic 102. In some embodiments, the periphery 110 comprises a single material that, apart from the subsurface layer 120, is homogeneous throughout. Alternatively, the subsurface layer 120 may form a separation between two different materials that form the periphery 110.

In some embodiments, the subsurface layer 120 is configured to scatter an amount of light that is at least twice the amount of light scattered by portions of the material adjacent the subsurface layer 120, more preferably at least 4 times the amount of light scattered by portions of the material adjacent the subsurface layer 120, and even more preferably 10 times the amount of light scattered by portions of the material adjacent the subsurface layer 120. In other embodiments, the subsurface layer 120 is configured to scatter an amount of light that is at least twice the amount of light scattered by an intraocular lens that does not have a subsurface layer such as the subsurface layer 120, but which is otherwise substantially equivalent to the intraocular lens 100. In yet other embodiments, the subsurface layer 120 is configured to scatter an amount of light that is at least 4 times, more preferably 10 times the amount of light scattered by an intraocular lens that does not have a subsurface layer such as the subsurface layer 120, but which is otherwise substantially equivalent to the intraocular lens 100. In some embodiments, the amount of light scattered by the subsurface layer 120 is determined by illuminating at least a portion of the subsurface layer 120 with a beam of light, such as a laser beam, and measuring the amount of light received by a photodetector having a predetermined area and disposed, for example, 10 centimeter to 1 meter or more from the intraocular lens 100. The amount of light received by the photodetector may then be compared to the amount of light received by the photodetector under a reference condition, for example, by removing the intraocular lens 100 or replacing the intraocular lens 100 by an intraocular lens that does not have a subsurface layer, but which is otherwise substantially equivalent to the intraocular lens 100.

As illustrated in FIG. 1, the subsurface layer 120 may form a contiguous strip that completely surrounds the central portion 148 of the optic 102. This configuration of the subsurface layer 120 advantageously scatters light intercepting the periphery region 110 of the intraocular lens 100. Alternatively, the subsurface layer 120 may be circumferentially broken along one or more regions.

In FIG. 3, the subsurface layer 120 is disposed within a plane that is orthogonal to the optical axis OA and has a radial width L1 in a direction away from or perpendicular to the optical axis OA. In some embodiments, the radial width L1 of the subsurface layer 120 may be clearly delineated by distinct inner and outer edges. In other embodiments, the radial width L1 may be estimated if inner and/or outer edges are less distinct, for example, if the subsurface layer 120 has a scattering cross-section that is a Gaussian in a radial direction. The thickness of the subsurface layer 120 in a direction along the optical axis OA may be relatively thin, as shown in FIG. 3, or may be thicker in order to increase the scattering cross-section of the subsurface layer 120. Generally, the radial width L1 is greater than about four times the thickness. In certain embodiments, the radial width is at least 100 micrometers, while in other embodiments, the radial width L1 is at least 200 micrometers, 500 micrometers, or 1 millimeter or more.

The subsurface layer 120 may be disposed at or near the top surface 112 of the peripheral region 110, as illustrated in FIG. 3. Alternatively, the subsurface layer may be disposed at other depths beneath the top surface 112, for example, at or near the bottom surface 114 or approximately equidistant between the surfaces 112, 114. The location will generally be predicated on such factors as ease of fabrication or scattering characteristics as a function of layer depth.

Figure 10A:
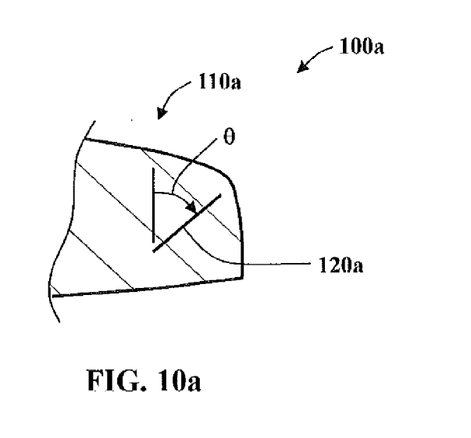
FIGS. 10a-e are side views of intraocular lenses illustrating various embodiments of a subsurface layer or layers for scattering incident light.
Figure 10B:
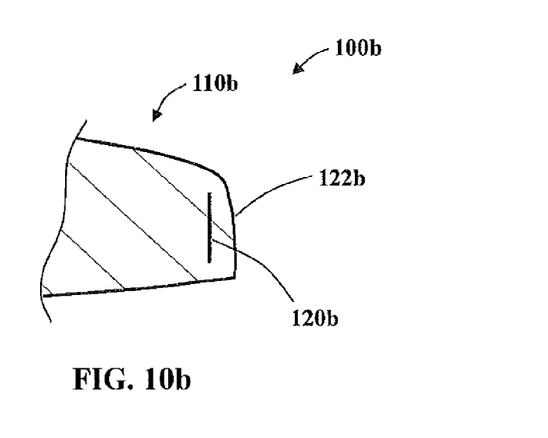
Figure 10C:
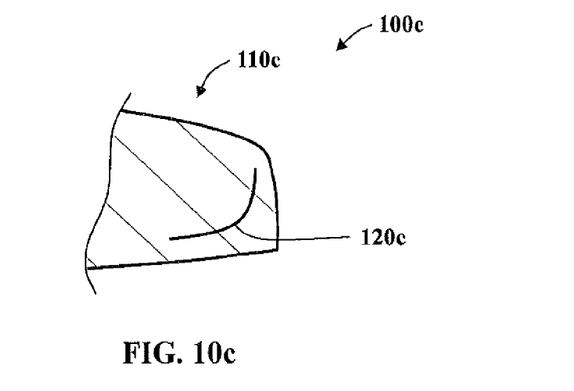

Other configurations and distributions of the subsurface layer 120 besides that illustrated in FIG. 3 are possible. For example, in FIG. 10a, an intraocular lens 100a comprises a peripheral region 110a having a subsurface layer 120a that forms a conic section in which the subsurface layer 120a is oriented at an angle relative to the optical axis OA. The angle θ may be selected to provide a particular light scattering characteristic (e.g., scattering cross-section or angular distribution of the light scattered) that reduces the amount of glare produced by peripheral light. Referring to FIG. 10b, an intraocular lens 100b comprises a peripheral region 110b having a subsurface layer 120b that is disposed to form a cylindrical surface that is oriented parallel to an optical axis or an outer surface 122b. Referring to FIG. 10c, an intraocular lens 100c comprises a peripheral region 110c having a subsurface layer 120c that is disposed to form an arcuate shape when viewed in cross-section in a plane congruent with the optical axis OA.

Figure 10D:
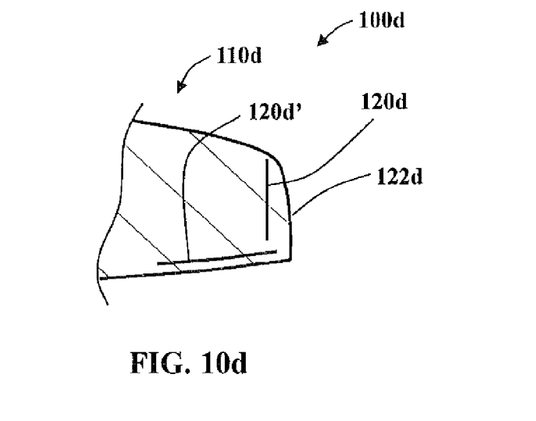
Figure 10E:
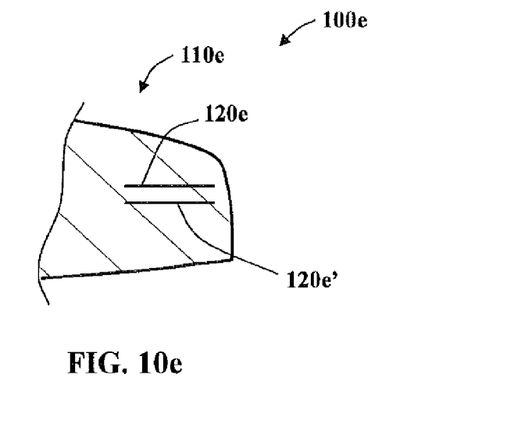

Referring to FIG. 10d, in certain embodiments, an intraocular lens 100d comprises a peripheral region 110d having at least two subsurface layers 120d and 120d' configured to provide a predetermined scattering characteristic, for example, causing light entering the peripheral region 110d to be multiply scattered. In the illustrated embodiment, the subsurface layer 120d' is parallel to an optical axis of the intraocular lens 100d, while the subsurface layer 120d is perpendicular to the optical axis. In such embodiments, at least some of the light directed toward an outer surface 122d of the peripheral edge 110d is reflected and scattered by the subsurface layer 12d. At least some of the reflected light is subsequently diffusely scattered by the subsurface layer 120d'. Referring to FIG. 10e, an intraocular lens 100e comprises at least two subsurface layers 120e, 120e' that are disposed parallel to one another so that at least some of the light entering the peripheral region 110 is twice scattered, first by the subsurface 120d and then by the subsurface 120d'. Additional subsurface layers may be used to further increase the amount of light scattered and/or to increase the scattering cross-section for light entering the peripheral region at one or more specific angles or ranges of angles. For example, the subsurface layers 120d, 120d' or 120e, 120e' may be configured to scatter at least twice the amount of light that would be scattered by the surface 120d or 120e alone if illuminated by a beam of light. In some embodiments, two or more subsurface layers are configured at one or more angles relative to an optical axis (similar to the subsurface layer 120a in FIG. 10a) or have a arcuate or more complex shape (similar to the subsurface layer 120c in FIG. 10c).

The subsurface layer 120 may comprise a variety of characteristics and mechanisms for scattering light in a predetermined manner. In some embodiments, the subsurface layer 120 comprises a variation in refractive index of the material within the layer. The refractive index variations may be random or pseudo-random in nature or may be more systematically structured to scatter light in one or more preferred directions or with a predetermined angular distribution. The subsurface layer 120 may be configured so that the refractive index variations are along one axis or along multiple axes, for example, in one or two directions along the subsurface layer 120 and/or in a direction normal to the subsurface layer 120. The variation in refractive index in one or more directions may be continuous and/or characterized by localized micro-discontinuities. For example, the refractive index variation in one or more directions may be in the form of a plurality of small voids, opaque particles or spots, and/or localized material changes in the intraocular lens material. In general, the size of such discontinuities is preferably on the order of a wavelength of visible light, for example, about 2 micrometers or less, about 1 micrometer or less, or about 500 nanometers or less.

In some embodiments, the subsurface layer 120 may be configured for alternative or additional purposes beside the purpose of preventing or reducing glare on the retina. For example, the subsurface layer 120 may be formed to produce one or more shapes that may be used to identify the intraocular lens 100. In such embodiments, the subsurface layer 120 may be configured to form of one or more alphanumeric characters, symbols, or geometric shapes such as squares, rectangles, triangles, circles, or ellipses. Alternatively or additionally, one or more subsurface layers may be configured to assist a practitioner to orient the intraocular lens 100 prior to and/or after placement within the eye of a subject. One example of such features to orient an intraocular lens is found in US Patent Application Number 2005/149184, which is herein incorporated by reference.

Figure 11:
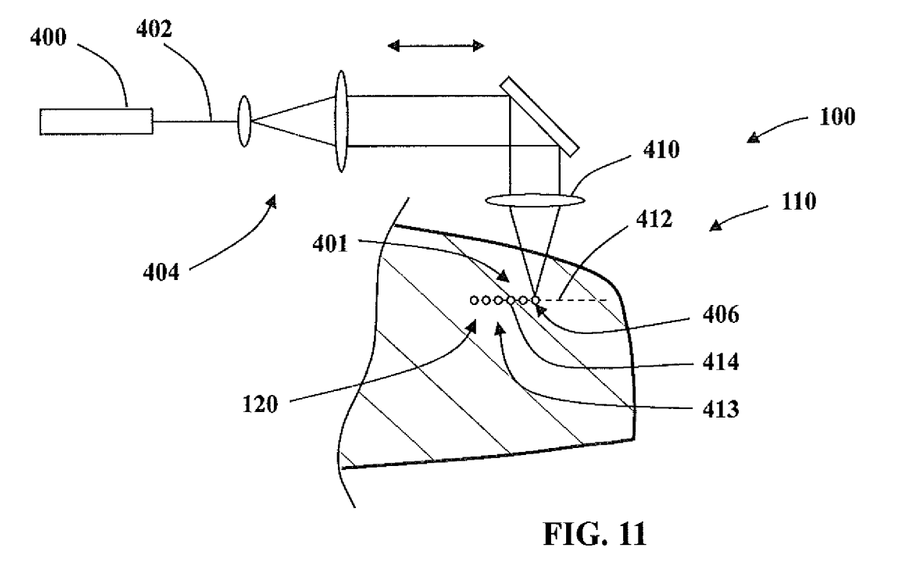
FIG. 11 is a side view of an intraocular lens showing a laser configured to produce a subsurface layer within the intraocular lens.

Referring to FIG. 11, in certain embodiments, a method of producing the subsurface layer 120 comprises providing a laser 400 and using the laser to form a plasma within an interior portion 401 of the intraocular lens 100, for example, within the peripheral region 110. The laser 400 may be any laser providing a beam that can be sufficiently focused to produce a plasma, for example, a near infrared (NIR), ultra-short pulse laser such as the experimental system described by Leander Zickler, et al. in "Femtosecond All-Solid State Laser for Refractive Surgery" (Commercial and Biomedical Applications of Ultrafast Lasers III, Proceedings of SPIE, Vol. 4978 (2003)), which is herein incorporated by reference. Alternatively, the laser 400 may comprise a commercial system such as the Coherent RegA 9000/9050 Ti: Sapphire regenerative amplifier available from Coherent Inc. (Santa Clara, Calif., USA) or the IMRA FCPA microjoule D-1000 Ytterbium fiber oscillator/amplifier laser system available from IMRA America Inc. (Ann Arbor, Mich., USA) or high-repetition rate, cavity dumped, mode-locked ultrafast laser systems such as femtoNOVA available from High Q Laser Production GmbH (Hohenems, Austria). In certain embodiments, the laser 400 is able to produce a pulse sequence of pulses having pulse widths of 10 to 100,000 femtoseconds, minimum pulse energies of 0.1 nJ to 100 micojoules, temporal pulse separations of 10 ns to 100 microseconds, at a laser wavelength of 200 nm to 2 microns. The use of lasers for this type of material processing are described in greater detail in, for example, U.S. Pat. No. RE 37,585, which is herein incorporated by reference.

The laser 400 may be used to produce a beam 402 of light that is expanded using expansion optics 404. Light from the beam 402 is directed to at least one focus 406 within the interior portion 401 using a lens 410. The focus 406 preferably has a spot size ranging from about 1 to about 100 microns. Alternatively, the single lens 410 may be replaced by some other optical element or optical system suitable for focusing laser light such as a mirror, a diffractive optical element, or some combination of lenses, mirrors, and/or diffractive optical elements that form a focus or a plurality of foci. Preferably, the optical systems used to create the focus 406 that creates a high energy density within a relatively small volume, for example, by configuring the optical system to have a high numerical aperture (NA). In certain embodiments, the NA is between about 0.25 and about 1.2, preferably greater than 0.5 or greater than 0.8, even more preferably greater than or equal to about 1.

The laser light contained in the focus 406 provides an energy or power density that is sufficient to produce a plasma within the interior portion 401. An exemplary laser system for producing such a plasma is discussed by Leander Zickler in the Proceedings of SPIE, Vol. 4978 (2003) publication cited above herein. Generally, the subsurface layer 120 is formed as a condition of laser-induced optical breakdown occurs within the material inside the interior portion 401. As the laser 400 is a pulsed, the laser pulses create a plurality 413 of localized micro-discontinuities 414, each of the micro-discontinuities 414 having an overall or average refractive index or effective refractive index that is different from that of the surrounding material.

In some embodiments, each of the micro-discontinuities 414 is in the form of a small volume in which the refractive index is substantially constant, but is different from the refractive index of material adjacent the subsurface layer 120. In other embodiments, the refractive index within a micro-discontinuity 414 varies, for example, having a higher refractive index in the center and a refractive index at a periphery that approaches or is substantially equal to the refractive index of adjacent material. In yet other embodiments, the micro-discontinuities 414 comprise small cavities or voids that forms within the interior portion 401 of the intraocular lens 100.

In general, the localized difference in refractive index or effective refractive index of the micro-discontinuities 414 causes light incident to refract in a different direction or directions. The combined effect of the plurality 413 of micro-discontinuities 414 is that at least some of the light incident upon the subsurface layer 120 is scattered in a different direction. In some embodiments, the subsurface layer 120 is configured to produce a random or quasi-random scattering distribution of incident light by randomly or quasi-randomly varying one or more properties of different micro-discontinuities 414. The variation in property may include, but not be limited to, the size of the micro-discontinuities 414, the refractive index of the micro-discontinuities 414, and the spacing between adjacent micro-discontinuities 414. In addition, the plurality 413 of micro-discontinuities 414 can be distributed at varying depths within the interior portion 401 to produce multiple scattering of light incident upon the subsurface layer 120. In some embodiments, the absorption or transmissivity of the micro-discontinuities 414 may also be varied compared to the surrounding material or compared to one another.

The method of producing the subsurface layer 120 further comprises moving the focus 406 within the interior portion 401 so as to from an extended area with a predetermined extent and scattering cross-section. The extent, shape, number of the subsurface layer(s) 120 formed by the focus 406 may be any of those illustrated and discussed herein, such as those illustrated in FIGS. 1, 3, and 10a-e, or any other form suited to provide a desired scattering characteristic or cross-section.

The subsurface layer 120 may be formed by moving the focus 406 and/or intraocular lens 100 relative to one another by using, for example, a scanning mirror, translation stage, and/or rotation stage that is under computer control to provide a predetermined pattern. In certain embodiments, hardware and control mechanisms similar to those used in performing a LASIK or similar surgical procedures may in adapted for use in the present application of forming the subsurface layer 120. As an example for such system, the IntraLase Pulsion FS60 available from IntraLase Inc. (Irvine, Calif., USA), is cited. In the illustrated embodiment in FIG. 11, the focus 406 moves along a straight line portion 412 and then indexed circumferentially along a new line 412' (not shown). Alternatively, the focus 406 may be moved in a more complex pattern along the surface layer 120 being formed by the laser 400, for example in a pattern similar to those used in modifying the corneal surface in a LASIK surgical procedure. In some embodiments, several passes may be made over the same position or area in order to provide subsurface layer 120 with a particular scattering characteristic. In addition, several passes may be made at varying depths within the interior portion in order to increase the thickness of the subsurface layer 120.

In some embodiments, the micro-discontinuities 414 are evenly distributed, as illustrated in FIG. 11. Alternatively, the micro-discontinuities 414 may be randomly distributed within the plane of the subsurface layer 120 and/or along the thickness of the subsurface layer 120. In addition, the density of the micro-discontinuities 414 may be either constant throughout the subsurface layer 120 or may vary over portions of the subsurface layer 120. For example, the micro-discontinuities 414 may be evenly distributed within a central portion or along an annular portion of the subsurface layer 120, while density of the micro-discontinuities 414 near boundary portions of the subsurface layer 120 may decrease, for example as a Gaussian function.

In certain embodiments, the subsurface layer 120 may be configured to systematically vary the refractive index or transmissivity along the surface in way that causes incident light to produce an interference pattern that diffracts or scatters at least some the incident light in a predetermined manner. This variation may be constructed to redirect a predetermined portion of the light (e.g., light at a particular wavelength or range of wavelengths) in a particular direction so as to prevent or reduce the formation of glare patterns on the retina. Additionally or alternatively, the variation may be configured to cause incident light to scatter with a predetermined angular distribution.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:
1. An intraocular lens, comprising:
an optic disposed about an optical axis comprising an anterior surface and an opposing posterior surface, the surfaces configured to focus light when implanted within a capsular bag of an eye;

a support structure coupled to the optic; and a textured surface disposed over a surface portion of the intraocular lens, the textured surface comprising a plurality of repetitive, periodically-spaced protrusions disposed over a base surface, each protrusion having a smooth distal face and a sharp corner edge having a radius of less than about 100 nanometers;

wherein the smooth distal faces have a roughness less than about 200 nanometers, and the base surface has a roughness that is greater than the roughness of the smooth distal faces.

2. The intraocular lens of claim 1, wherein the smooth distal faces have an arithmetical average roughness that is less than about 50 nanometers.

3. The intraocular lens of claim 1, wherein the protrusions extend from the surface portion by an amount that is about 0.5 micrometers.

4. The intraocular lens of claim 1, wherein the support structure comprises a haptic, the textured surface disposed upon at least a portion of the haptic.

5. The intraocular lens of claim 4, wherein the textured surface is disposed at least upon a posterior surface of the haptic, the posterior surface configured to engage a posterior capsule of the capsular bag.

6. The intraocular lens of claim 1, further comprising a periphery disposed about the optical axis, the textured surface disposed at least within a portion of the periphery.

7. The intraocular lens of claim 1, wherein the support structure comprises a flexible positioning member coupled to the optic, the flexible positioning member having an outer surface configured to engage the capsular bag, the textured surface disposed over at least a portion of the outer surface.

8. The intraocular lens of claim 1, wherein the support structure comprises a flexible bag having an outer surface, the flexible bag being filled with a resilient fill material and configured to deform in response to an force.

9. The intraocular lens of claim 1, wherein the textured surface further comprises a plurality of pillars.

10. The intraocular lens of claim 9, wherein the smooth distal face is circular.

11. The intraocular lens of claim 1, wherein the each protrusion further comprises a side wall, the sharp corner edge being formed along an intersection of the side wall and the smooth distal face.

12. The intraocular lens of claim 11, wherein the side wall and the smooth distal face form an angle that is between about 60 degrees and about 120 degrees.

13. The intraocular lens of claim 1, wherein the smooth distal faces each have a face width and are disposed with a center-to-center spacing between adjacent smooth distal faces, the face width being between about 1 micrometer and about 4 micrometers and the center-to-center spacing being between about 2 micrometers and about 8 micrometers.

14. The intraocular lens of claim 13, wherein the center-to-center spacing is about twice the face width.

15. The intraocular lens of claim 13, wherein the ratio of the face width to the center-to-center spacing is between about 0.4 and 0.7.

16. The intraocular lens of claim 1, wherein the textured surface is configured to adhere to a wall of the capsular bag.

17. The intraocular lens of claim 1, wherein the textured surface is configured to cause optical interference of an impinging wavefront.

18. The intraocular lens of claim 1, wherein the protrusions are smooth ridges and the smooth ridges are separated by channels.

19. The intraocular lens of claim 18, wherein the channels have a depth that is less than 0.5 micrometers and a center-to-center spacing between adjacent ridges is between about 2 micrometers and about 8 micrometers.

20. The intraocular lens of claim 18, wherein the channels have a depth that is less than 0.5 micrometers.

21. The intraocular lens of claim 19, wherein the smooth ridges have a ridge width and the ratio of the ridge width to the center-to-center spacing is between about 0.4 and 0.7.

22. The intraocular lens of claim 18, wherein the extent of the plurality of channels in a direction normal to a length of the channels is between about 100 micrometers and about 1 millimeter.

23. The intraocular lens of claim 18, wherein the protrusions and the channels are concentrically disposed about the optical axis.

24. The intraocular lens of claim 1, wherein the textured surface is configured to form a mono-layer of cells adjacent the textured surface when the intraocular lens is placed in the eye.

25. The intraocular lens of claim 1, further comprising a periphery disposed about the optical axis comprising a single material and including a top surface, a bottom surface, and a subsurface layer disposed therebetween, the subsurface layer configured to scatter an amount of light that is at least twice the amount of light scattered by portions of the material adjacent the subsurface layer or at least twice the amount of light scattered by another intraocular lens that does not have the subsurface layer, but which is otherwise substantially equivalent.

26. An intraocular lens, comprising:

an optic disposed about an optical axis comprising an anterior surface and an opposing posterior surface, the surfaces configured to focus light when implanted within a capsular bag of an eye;

a support structure coupled to the optic; and a textured surface disposed over a surface portion of the intraocular lens, the textured surface comprising a plurality of repetitive, periodically-spaced protrusions, each protrusion having a smooth distal face having a roughness less than about 200 nanometers, wherein the smooth distal faces each have a face width and are disposed with a center-to-center spacing between adjacent smooth distal faces, and wherein each protrusion also includes a sharp corner edge having a radius of less than about 100 nanometers;

wherein the ratio of the face width to the center-to-center spacing is between about 0.4 and 0.7.

27. An intraocular lens, comprising:

an optic disposed about an optical axis comprising an anterior surface and an opposing posterior surface, the surfaces configured to focus light when implanted within a capsular bag of an eye;

a support structure coupled to the optic; and a textured surface disposed over a surface portion of the intraocular lens, the textured surface comprising a plurality of repetitive, periodically-spaced protrusions, each protrusion having a smooth distal face having a roughness less than about 200 nanometers, and wherein each protrusion also includes a sharp corner edge having a radius of less than about 100 nanometers;

wherein the protrusions are smooth ridges and the smooth ridges are separated by channels, wherein the channels have a depth that is less than or equal to about 0.5 micrometers.

* * * * *